US006444623B1

United States Patent
Wu et al.

(10) Patent No.: US 6,444,623 B1
(45) Date of Patent: Sep. 3, 2002

(54) METHODS FOR THE PRODUCTION OF SULFURIZED DIPHENYLOXIDES AND COMPOSITIONS MADE THEREFROM

(75) Inventors: Margaret M. Wu, Skillman, NJ (US); Philip Trotto, Yardley, PA (US); Rene B. LaPierre, Guilford, CT (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/473,556

(22) Filed: Dec. 29, 1999

Related U.S. Application Data

(60) Provisional application No. 60/114,243, filed on Dec. 30, 1998, and provisional application No. 60/114,244, filed on Dec. 30, 1998.

(51) Int. Cl.$^7$ .................... C10M 111/02; C07D 327/08
(52) U.S. Cl. ...................... 508/301; 508/300; 508/581; 549/16
(58) Field of Search ............................ 549/16; 508/300, 508/301, 581

(56) References Cited

U.S. PATENT DOCUMENTS

| | | | | |
|---|---|---|---|---|
| 3,975,403 A | * | 8/1976 | Gante et al. | 260/327 P |
| 5,286,396 A | * | 2/1994 | Rudnick et al. | 252/48.2 |
| 5,552,071 A | * | 9/1996 | Rudnick et al. | 508/581 |

OTHER PUBLICATIONS

Organic Syntheses, Collective Volume 2, by A.H. Blatt, pp. 485–486, 1943.

\* cited by examiner

*Primary Examiner*—Ellen M. McAvoy

(57) ABSTRACT

The present invention relates to methods for production of sulfurized diphenyloxides wherein a diphenyloxide is reacted with elemental sulfur in the presence of solid acid catalyst. The solid acid catalyst can be a zeolite or a catalytic amount of a Friedel-Crafts compound. The present invention further relates to a composition containing between about 40 and about 80 weight percent diphenyloxide; no more than about 15 weight percent diphenyloxide thiol; between about 5 and about 45 weight percent phenoxathiin; and between about 3 and about 50 weight percent total of bis (diphenyloxide) sulfide, diphenyloxide phenoxathiin sulfide, and bis(phenoxathiin) sulfide.

23 Claims, No Drawings

METHODS FOR THE PRODUCTION OF SULFURIZED DIPHENYLOXIDES AND COMPOSITIONS MADE THEREFROM

This Application claims benefit of U.S. provisional Application Ser. Nos. 60/114,243, filed Dec. 30, 1998, and 60/114,244, filed Dec. 30, 1998.

FIELD OF THE INVENTION

The present invention relates to methods for the production of sulfurized diphenyloxides and compositions made therefrom. In particular, the present invention relates to methods for the production of sulfurized diphenyloxides from the reaction of diphenyloxides with elemental sulfur in the presence of a solid acid catalyst. The solid acid catalyst can be a zeolite or a catalytic amount of a Friedel-Crafts compound. Compositions made from the sulfurized diphenyloxides are useful as lubricant base stocks and additives thereto.

BACKGROUND OF THE INVENTION

Sulfurized diphenyloxides are beneficial as lubricant additives, lubricant base stocks, or intermediates to lubricant base stocks. Sulfurized diphenyloxides include, for example, phenoxathiin, bis(diphenyloxide) sulfides, diphenyloxide phenoxathiin sulfides, and bis(phenoxathiin) sulfides having the structures shown below. Alkylated phenoxathiin is a high-performance synthetic lube base stock with excellent viscometrics, oxidative stability, and antiwear properties. In addition, the bis(diphenyloxide) sulfide has been reported as a high-performance fluid.

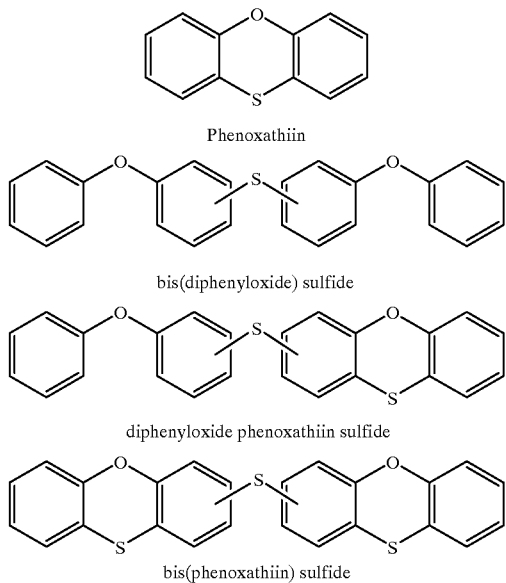

Phenoxathiin bis(diphenyloxide) sulfide diphenyloxide phenoxathiin sulfide bis(phenoxathiin) sulfide Sulfurized diphenyloxides can be prepared from the reaction of diphenyloxide with sulfur using stoichiometric amounts of $AlCl_3$ at low temperatures. The reaction is believed to proceed through an aromatic electrophilic substitution mechanism. The acid catalyst enhances the electrophilicity of sulfur via the formation of positively charged sulfur intermediates. These intermediates are believed to be produced by the formation of a Lewis acid-base adduct between sulfur and the Lewis acid or by the protonation of sulfur by a Bronsted acid. However, the use of stoichiometric amounts of $AlCl_3$ does not provide an adequate commercial source of sulfurized diphenyloxides. Rather, the known process suffers from numerous drawbacks, including, for example, the use of corrosive reactants (e.g., halogenated hydrocarbons), the production of corrosive by-products (e.g., gaseous hydrochloric acid), poor selectivity (e.g., the production of significant amounts of higher sulfurized diphenyloxides, such as diphenyloxide phenoxathiin sulfide), and the need for extensive downstream separations (e.g., separation of catalyst from the product stream).

These drawbacks have negative implications for the commercial use of sulfurized diphenyloxides. The commercial use of sulfurized diphenyloxides has been hampered by the need to purify the sulfurized diphenyloxide prior to use. In particular, the presence of high concentrations of corrosive by-products has made it imperative that the sulfurized diphenyloxides be removed from the product stream prior to use. However, the purification of the sulfurized diphenyloxides is expensive and time consuming.

Accordingly, it would be highly beneficial to provide methods for the large scale production of sulfurized diphenyloxides. The method should provide for the production of sulfurized diphenyloxides in large yield without the use of highly corrosive reactants. Further, the method should produce little or no corrosive and/or undesired by-products. In addition, the method should utilize readily available reactants and be selective.

SUMMARY OF THE INVENTION

The drawbacks associated with the known method for producing sulfurized diphenyloxides is overcome, to a large extent, by methods in accordance with the present invention. The present invention provides a method for producing sulfurized diphenyloxides wherein a diphenyloxide and elemental sulfur are reacted in the presence of a solid acid catalyst. The reaction is very clean and produces little undesirable by-products. Usually, high sulfur conversion and selectivity to specific sulfurized diphenyloxides can be obtained under mild reaction conditions. The method can be used to produce sulfurized diphenyloxides in large scale and at economical prices.

In one of its aspects, the present invention relates to methods for the production of a sulfurized diphenyloxide wherein a diphenyloxide is reacted with elemental sulfur in the presence of a solid acid/oxide catalyst. In one embodiment, the diphenyloxide is alkylated prior to reaction with sulfur. Alternatively, alkylation is performed after sulfurization of the diphenyloxide. Preferably, however, the sulfurization and alkylation occur concurrently. In one embodiment, the acid catalyst comprises a molecular sieve, preferably a zeolite such as MCM-56, ZSM-5, MCM-22, MCM-68, and USY. Alternatively, the catalyst comprises a catalytic amount of a Friedel-Crafts compound, such as $AlCl_3$. When the catalyst comprises a Friedel-Crafts compound, the reaction is preferably conducted at a temperature above about 75° C., more preferably at a temperature above about 120° C., and even more preferably at a temperature above about 180° C.

In another of its aspects, the present invention relates to a composition comprising between about 40 and about 80 weight percent diphenyloxide; no more than about 15 weight percent diphenyloxide thiol; between about 5 and about 45 weight percent phenoxathiin; and between about 3 and about 50 weight percent total of bis(diphenyloxide) sulfide, diphenyloxide phenoxathiin sulfide, and bis(phenoxathiin) sulfide.

Additional features and embodiments of the present invention will become apparent to those skilled in the art in view of the ensuing disclosure and appended claims.

DETAILED DESCRIPTION OF THE INVENTION

The present invention relates to methods for the production of sulfurized diphenyloxides. The sulfurized diphenyloxides are produced by reacting a diphenyloxide with elemental sulfur in the presence of a solid acid catalyst according to reaction Scheme 1 below. It will be appreciated by those skilled in the art that the diphenyloxide can be optionally alkylated on one or both of the phenyl groups prior to reaction with the sulfur. The methods enable the production of a variety of sulfurized diphenyloxides, including phenoxathiin, bis(diphenyloxide) sulfide, diphenyloxide phenoxathiin sulfide, and bis(phenoxathiin) sulfide. Additionally, the methods can be used to produce substituted sulfurized diphenyloxides, including alkylated phenoxathiins.

Scheme 1

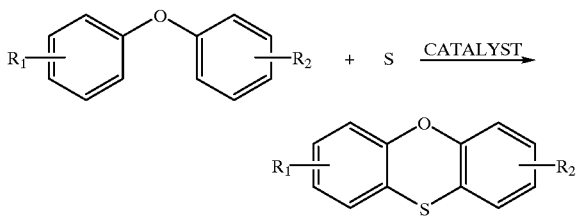

wherein $R_1$ and $R_2$ are individually H or an alkyl group.

The sulfur is in its elemental form and can be used without further purification. The sulfur can be combined with the diphenyloxide to form a saturated sulfur solution. Toward that end, the sulfur can be dissolved within a liquid solution containing the diphenyloxide. For example, an appropriate amount of sulfur can be dissolved directly in an appropriate amount of diphenyloxide to provide a diphenyloxide/sulfur solution having the desired mole ratio of diphenyloxide to sulfur. Preferably, the diphenyloxide/sulfur solution is saturated with sulfur.

The reaction between the diphenyloxide and the sulfur is carried out in the presence of solid acid catalyst. The acid catalyst can be aluminum chloride ($AlCl_3$), $BF_3$, $AlBr_3$, solid zeolite, a layered catalyst, or any of a variety of other molecular sieves. Examples of suitable zeolite catalysts include MCM-56, ZSM-5, MCM-22, MCM-68, and USY. Zeolites may be used with framework metal elements other than aluminum such as, for example, boron, gallium, iron, and chromium.

When a zeolite is used, the zeolite preferably has a pore size of at least 5 Å. Large pore size zeolite catalysts are usually preferred, although less highly constrained medium or intermediate pore size zeolites may also be used. Generally, the large pore size zeolites are characterized by a pore structure with a ring opening of at least about 7 Å and the medium or intermediate pore size zeolites with a ring structure of 10 membered oxygen ring systems will have a pore opening smaller than about 7 Å but larger than about 5.6 Å. Examples of suitable large pore size zeolites include faujasite, synthetic faujasites (zeolite X and Y), zeolite L, ZSM4, ZSM-18, ZSM-20, mordinite and offretite which are characterized by the presence of a 12-membered oxygen ring system in the molecular structure as described in Chen et al., "Shape-Selective Catalysis in Industrial Applications", Chemical Industries Vol. 36, Marcel Dekker Inc., New York, 1989. The large pore zeolites are preferably characterized by a "Constraint Index" of not more than 2, in most cases not more than 1. Zeolite beta is included in this class although it may have a "Constraint Index" approaching the upper limit of 2. The method for determining Constraint Index is described in U.S. Pat. No. 4,016,218 together with values for typical zeolites. The significance of the Constraint Index is described in U.S. Pat. No. 4,816,932 to which reference is made for a description of the test procedure and its interpretation.

A highly useful large pore zeolite for the production of the sulfurized diphenyloxides of the invention is zeolite Y in the ultrastable form, usually referred to as USY. Zeolite USY or zeolite Y, is a material of commerce, available from W. R. Grace & Co. and other suppliers, in large quantities as a catalyst for the cracking of petroleum. Zeolite Y may be bound with silica, alumina, silica-alumina or other metal oxides. It may typically have a $SiO_2^-$ to $Al_2O_3$ ratio of from 3–500, and be partially exchanged with rare earth elements, with ammonium cation or with other cations. Reference is made to Wojoiechowski, "Catalytic Cracking: Catalysts, Chemistry and Kinetics", Chemical Industries Vol. 25, Marcel Dekker, New York, 1986, for a description of zeolite USY, its preparation and properties.

Examples of useful medium pore size zeolites include the pentasil zeolites such as ZSM-5, ZSM-22, ZSM-23, and ZSM-35, as well as other zeolites such as ZSM-50, ZSM-57, MCM-22, MCM-49, MCM-56, MCM-68, all of which are known materials. Zeolite MCM-22 is described, for example, in U.S. Pat. No. 4,954,325 to M. K. Rubin and P. Chu. MCM-56 is described, for example, in U.S. Pat. Nos. 5,632,697; 5,453,554; 5,557,024; 5,536,894; and 5,827,491. MCM-68 is described, for example, in U.S. application Ser. No. 09/234,544, filed Jan. 21, 1999. All of the above patents and applications are hereby incorporated by reference in their entireties.

The zeolite catalyst is optionally pretreated. Pretreatment of the catalyst flows from the discovery that zeolite catalysts which are low in moisture content, water-of-hydration content and absorbed-oxygen content consistently produce compositions that have improved color and excellent oxidative and thermal stability. Commercially obtained zeolite catalysts have been found to be relatively rich in moisture content, water-of-hydration content and absorbed-oxygen content. Reducing the moisture content, water-of-hydration content and absorbed-oxygen content of the commercially obtained zeolite catalyst by pretreatment has been found to yield a superior product.

The zeolite catalyst is pretreated by heating the solid catalyst particles for a time sufficient to lower the catalyst water content, water-of-hydration and absorbed oxygen content. Preferably and conveniently, the solid catalyst is heated in a vessel in bulk form but it is within the scope of the present invention to suspend the catalyst in an otherwise unreactive and inert liquid, with or without stirring, to enhance heat transfer to the solid catalyst and accelerate pretreatment. Vapor of the inert liquid may be removed periodically to carry off water vapor and oxygen from the catalyst. However, the zeolite catalyst is pretreated preferably by heating the solid catalyst in an inert gaseous environment at a temperature and for a time sufficient to lower the catalyst water content, water-of-hydration and absorbed oxygen content. Most preferably, the pretreatment is carried out in a vessel employing a moisture-free inert gas purge stream, such as nitrogen or Group VIII gases of the Periodic Table, to remove water vapor and oxygen from the vessel. Optionally, the pretreatment may be carried out by heating the catalyst in vacuo in a closed vessel.

To those skilled in the chemical engineering arts, other means are well known to essentially dry solid particles by continuous or batchwise methods. These methods are included within the scope of the present invention to the extent that they can be applied to remove water, water-of-hydration and absorbed oxygen from solid zeolite catalyst particles. The zeolite catalyst can be pretreated in a fixed bed, fluid bed or batchwise. Rather than employing a vessel, the solid catalyst particles can be transported through a column containing an inert liquid at an appropriate temperature or the solid can be carried through a heated or inert liquid-containing column by gas ebullition.

The water content, water-of-hydration and absorbed oxygen content of the zeolite catalyst particles can be effectively lowered by heating the catalyst at a temperature between about 50° C. and about 500° C., but preferably at a temperature between about 200° C. and about 400° C. The catalyst is heated for between about 0.5 hours and about 24 hours and, preferably, between about 1 hour and about 5 hours. However, at a preferred temperature of about 300° C. in a vessel in the presence of a nitrogen purge stream, about two hours of heating has been found sufficient to pretreat the catalyst particles.

As an alternative to the zeolites, other molecular sieves may be used. Examples of useful, non-zeolite molecular sieves include the silicates (e.g., metallosilicates, titanosilicates) of varying silica-alumina ratios; metalloaluminates (e.g., germaniumaluminates); metallophosphates; aluminophosphates (AlPO; e.g., the silico- and metalloaluminophosphates referred to as metal integrated aluminophosphates (MeAPO and ELAPO); metal integrated silicoaluminophosphates (e.g., MeAPSO and ELAPSO); and silicoaluminophosphates (SAPO)); and gallogermanates. Without intending to be bound by theory, it is believed that use of the non-zeolite molecular sieves may not be as favorable since it appears that some acidic activity (as conventionally measured by the alpha value) is desired for optimum performance. A discussion of the structural relationships of SAPOs, AlPOs, MeAPOs, and MeAPSOs may be found in a number of resources including *Stud. Surf Catal.*, 37:13–27 (1987). The AlPOs contain aluminum and phosphorus, while in the SAPOs some of the phosphorus and/or some of both the phosphorus and aluminum is replaced by silicon. In the MeAPOs, various metals are present, such as Li, B, Be, Mg, Ti, , Fe, Co, An, Ga, Ge, and As, in addition to aluminum and phosphorus, while the MeAPSOs additionally contain silicon. The negative charge of the $Me_aAl_bP_cSi_dO_e$ lattice is compensated by cations, where Me is magnesium, manganese, cobalt, iron, and/or zinc. MeAPSOs are described in U.S. Pat. No. 4,793,984. SAPO-type sieve materials are described in U.S. Pat. No. 4,440,871. MeAPO-type catalysts are described in U.S. Pat. Nos. 4,544,143 and 4,567,029. ELAPO catalysts are described in U.S. Pat. No. 4,500,651 and ELAPSO catalysts are described in European Patent Application No. 159,624. Specific molecular sieves are described, for example, in the following patents: MgAPSO and MgAPSO in U.S. Pat. No. 4,758,419; MnAPSO in U.S. Pat. No. 4,686,092; CoAPSO in U.S. Pat. No. 4,744,970; FeAPSO in U.S. Pat. No. 4,683,217; and ZnAPSO in U.S. Pat. No. 4,935,216. All of the above patents and applications are hereby incorporated by reference in their entireties. Specific silicoaluminumphosphates which may be used include SAPO-1 1, SAPO-17, SAPO-34, and SAPO-37. Other specific sieve materials include MeAPO-5 and MeAPSO-5.

The method of the invention is carried out by contacting the diphenyloxide, sulfur, and the catalyst in a suitable reaction zone which may be a fixed catalyst bed, fluid bed or stirred reactor vessel. The mole ratio of the diphenyloxide to sulfur is preferably between about 50:1 and about 0.1:1 and, more preferably, between about 25:1 and about 10:1, to provide sufficient diluent for the reaction. A mole ratio of higher than about 50:1 detrimentally affects the reaction by dilution. If the mole ratio is below about 1:1, excess unreacted diphenyloxide may remain.

The time for which the diphenyloxide and the sulfur are contacted can vary. In general, contact is maintained for a time sufficient that the diphenyloxide and the sulfur react to a desired level of completion. For example, contacting time can vary from several minutes to several hours or more.

The temperature which is maintained during the reaction of the diphenyloxide and the sulfur can also vary. In general, it is preferred to carry out the reaction at the lowest temperature which will provide for the desired efficiency of reaction. For example, suitable temperatures can range from about 20° C. to about 300° C. Preferably, when a zeolite catalyst is used, the reaction is carried out at, or slightly above, ambient room temperature. "Room temperature", as used herein, includes temperatures from about 20° C. to about 30° C., preferably about 25° C. When the catalyst comprises a Friedel-Crafts compound such as $AlCl_3$, the reaction is preferably conducted at a temperature above about 75° C., more preferably at a temperature above about 120° C., and even more preferably above about 180° C.

The pressure maintained during the reaction between the diphenyloxide and the sulfur can also vary. Appropriate pressures to provide efficient formation of sulfurized diphenyloxide product can be readily determined by one of skill in the art. For example, suitable pressures can range from about ambient pressure to about autogenous reaction pressure at the selected temperature. However, higher pressures can be used, for example up to about 1000 psig (68 atm) Preferably, the pressure is between about 400 psig (27.2 atm) and about 600 psig (40.8 atm).

The fixed bed weight hourly space velocity (WHSV) can also be varied. Appropriate values for the WHSV are between about 0.0 $hr^{-1}$ and about 10 $hr^{-1}$, preferably between about 0.1 $hr^{-1}$ and about 2 $hr^{-1}$, and more preferably between about 0.1 $hr^{-1}$ and about 1 $hr^{-1}$. A WHSV above about 10 $hr^{-1}$ is detrimental because of the short residence time. A WHSV below about 0.01 $hr^{-1}$ results in low productivity.

Alkylated sulfurized diphenyloxides can be prepared by introducing an alkylating agent into the reaction zone. The alkylating agent can be present in the reaction zone before, after, or while the diphenyloxide is contacted with the sulfur. Preferably, the alkylating agent is present during the sulfurization step so that diphenyloxides are produced from diphenyloxides in a single step. The alkylating agent is preferably an olefin, more preferably a $C_6$ to $C_{20}$ olefin, and most preferably a $C_{10}$ to $C_{18}$ alpha olefin such as dodecene-1, decene-1, and tetradecene-1.

Once the diphenyloxide, the elemental sulfur, and the optional alkylating agent have reacted to the desired level of completion, the resulting product mixture can optionally be purified. Preferably, the catalyst is removed from the product mixture. When a zeolite catalyst is used, the catalyst can be separated from the product mixture by, for example, filtration. When a Friedel-Crafts compound such as $AlCl_3$ is used, the catalyst can be separated by, for example, washing the product mixture with a suitable solvent (e.g., water).

The product mixture can also be treated to separate specific sulfurized diphenyloxide products from the product mixture. For example, the product mixture will generally contain a mixture of sulfurized diphenyloxides such as phenoxathiin, bis(diphenyloxide) sulfide, diphenyloxide phenoxathiin sulfide, bis(phenoxathiin) sulfide, and higher sulfurized diphenyloxides. The phenoxathiin may be separated from the other components by conventional chemical processing techniques, such as by distilling the product mixture under vacuum. The bis(diphenyloxide) sulfide, diphenyloxide phenoxathiin sulfide, and bis(phenoxathiin) sulfide can then be separated from the higher sulfurized diphenyloxides also using conventional chemical processing techniques.

If further alkylation is desired (or if alkylation has not been previously performed), the sulfurized diphenyloxides are also optionally alkylated to produce alkylated sulfurized diphenyloxides. The alkylation can be performed individually on specific diphenyloxides which have been separated from the product mixture. Alternatively, the alkylation can be performed on the product mixture as a whole to produce a mixture of alkylated sulfurized diphenyloxides.

EXAMPLES

The reaction of diphenyloxide and elemental sulfur over five solid acid catalysts (4 zeolites and $AlCl_3$) was studied. Diphenyloxide was percolated through an $Al_2O_3$ column (activated at 500° C.) at ambient conditions prior to use. Sulfur powder (sublimed, 99.99%; Baker) was dried in an oven at 100° C. before use. The reactions were conducted in a round-bottom reaction flask. A saturated sulfur solution in diphenyloxide was prepared by mixing sulfur and diphenyloxide in proper proportions in a volumetric flask and stirring the slurry until a homogeneous solution was obtained at room temperature. The reaction flask was loaded with the saturated sulfur solution and 2.0 g catalyst in a powder form (60–80 mesh, with sand). The reactant mixture was heated to 300° C. under a continuous $N_2$ flow (approximately 100 mL/min). When the reactant mixture reached a temperature of 300° C., the $N_2$ flow was stopped and gas evolution was observed. The reaction was allowed to proceed for 16 hours or until gas evolution ceased. The product mixture was then cooled to room temperature. When the zeolite catalysts were used, the catalyst was removed by filtration. When the $AlCl_3$ catalyst was used, the $AlCl_3$ was removed by washing the mixture with water. The product mixture was distilled under vacuum to isolate phenoxathiin from the residual fraction which contained most of the higher sulfurized diphenyloxides. Material balances were started after a 24 hour lineout period.

The reaction product mixtures were analyzed using gas chromatography on a Varian 3700 Gas Chromatograph with a DB-1 column (60 m×0.33 mm×1 $\mu$m; J&W Scientific). In addition, gas chromatography-mass spectroscopy analyses were performed on an HP 5890 Series III Gas Chromatograph with an SPB-1 column (60 m×0.32 mm×$\mu$m; Supelco). Sulfur analyses were conducted with an HP 5890 Series II Plus GC instrument equipped with an Altech column (10 m×0.53 mm×1.2 $\mu$m) and a sulfur chemiluminescence detector (Sievers 355).

The zeolite catalysts utilized were MCM-56, ZSM-5, MCM-22 (both self-bound and alumina-bound), and USY. The physical properties of each of these catalysts are listed in Table 1. In particular, a commercial 65 weight percent/35 weight percent $ZSM-5/Al_2O_3$ extrudate catalyst prepared from ZSM-5 crystals with 55/1 bulk $SiO_2/Al_2O_3$ ratio was used without further treatment. An H-form MCM-56 catalyst sample was prepared from as-synthesized MCM-56, which was crystallized in a 30 gallon (113.5 L) autoclave. The as-synthesized MCM-56 with 19/1 bulk $SiO_2/Al_2O_3$ ratio was ammonium exchanged two times using ~1 M ammonium sulfate solution at an elevated temperature (49–66° C.), followed by hybrid calcination at 538° C. to remove organic templates. An H-form USY was prepared from ultrastabilized USY with 5.4 bulk $SiO_2/Al_2O_3$ ratio and 24.54 Å unit cell size via ammonium exchange at pH 3.5 for about 4 hours to remove any non-framework aluminum species. The pH was controlled during the exchange using 20% $H_2SO_4$ solution. The exchanged USY crystals were washed with water to remove residual sulfate ions, then dried and calcined in air at 538° C. for 3 hours to make an H-form USY sample. The final H-form USY sample had about 8.0 framework $SiO_2/Al_2O_3$ by $^{27}Al$ nuclear magnetic resonance (NMR) and 24.53 Å unit cell size.

TABLE 1

| Catalyst type: | $ZSM-5/Al_2O_3$ | MCM-56 | USY | MCM-22 | $MCM-22/Al_2O_3$ |
| --- | --- | --- | --- | --- | --- |
| Catalyst/binder ratio | 65/35 | — | — | | 65/35 |
| Catalyst $SiO_2/Al_2O_3$ | 55/1 | 19/1 | 8/1 | | 24/1 |
| Alpha, G 102 | 230 | — | 409 | | 294 |
| Alpha, G 101 | — | 141 | — | | — |
| BET surface area (m$^2$/g) | 376 | 451 | 841 | | 445 |
| zeolite surface area (m$^2$/g) | 219 | 274 | 779 | | 266 |
| matrix surface area (m$^2$/g) | 157 | 177 | 62 | | 179 |
| Na (ppm) | 180 | 130 | 4600 | | 68 |

TABLE 1-continued

| Catalyst type: | ZSM-5/Al$_2$O$_3$ | MCM-56 | USY | MCM-22 | MCM-22/Al$_2$O$_3$ |
|---|---|---|---|---|---|
| ash (weight %) | — | 96.4 | 95.2 | | — |
| Midas Order No. | 92-61842 | 96-62438 | 98-1209 | | 98-4763 |

The activities and selectivities of the catalysts studied are summarized in Table 2.

TABLE 2

| | Example: | | | | | | |
|---|---|---|---|---|---|---|---|
| | 1 | 2 | 3 | 4 | 5 | 6 | 7 |
| Catalyst type: | MCM-22 | MCM-22 | ZSM-5 | MCM-56 | USY | MCM-22/Al$_2$O$_3$ | AlCl$_3$ |
| Molar ratio:DPO/S | 2.0 | 1.0 | 1.0 | 1.0 | 1.0 | 1.0 | 1.0 |
| Reaction temperature (° C.) | 200 | 250 | 250 | 200 | 200 | 250 | 135 |
| Wt % catalyst | 5.4 | 5 | 5 | 5 | 5 | 5 | 4 |
| Reaction time (hrs) | 16 | 18 | 20 | 20 | 20 | 26 | 24 |
| DPO conversion (%) | 24.3 | 43.6 | 54.5 | 46.8 | 41.3 | 56.7 | 46.2 |
| Product Distribution (%) | | | | | | | |
| DPO | 75.7 | 56.4 | 45.5 | 53.2 | 58.7 | 43.3 | 53.8 |
| DPO-SH | 0.3 | 0 | 0.5 | 0.7 | 13.4 | 0.4 | 0 |
| PNX | 17.4 | 30.6 | 7.8 | 24.0 | 5.6 | 10.4 | 42.4 |
| A, B, C | 5.3 | 10.7 | 45.1 | 22.1 | 22.3 | 45.7 | 3.8 |
| other | 1.4 | 2.3 | 1.1 | 0 | 0 | 0.3 | 0 |
| Selectivity (%) | | | | | | | |
| DPO-SH | 1.2 | 0 | 0.9 | 1.5 | 32.4 | 0.7 | 0 |
| PNX | 71.5 | 70.3 | 14.3 | 51.3 | 13.5 | 18.3 | 91.8 |
| A, B, C | 21.6 | 24.4 | 82.8 | 47.2 | 54.0 | 80.5 | 8.2 |
| other | 5.7 | 5.3 | 2.0 | 0 | 0 | 0.5 | 0 |

DPO = diphenyloxide
DPO-SH = Diphenyloxide thiol
PNX = phenoxathiin
A = bis(diphenyloxide) sulfide
B = diphenyloxide phenoxathiin sulfide
C = bis(phenoxathiin) sulfide The data for examples 1 and 2 show that the selectivities to phenoxathiin was about 70% from diphenyloxide and sulfur using the MCM-22 self-bound catalyst. The data for examples 3 and 6 show that selectivity to higher sulfurized diphenyloxides were over 80% using ZSM-5 or MCM-22 alumina-bound catalysts.

Purified phenoxathiin and higher sulfurized diphenyloxides were alkylated by reaction with 1-tetradecene or 1-hexadecene over a USY catalyst. The properties of the alkylated phenoxathiin were measured and are summarized in Table 3. The measurements made on the alkylated diphenyloxide fluid are also shown in Table 3 as a comparative example. The examples demonstrate that alkylated phonxathiins isolated from Examples 2 and 7 have excellent oxidative stability, as indictaed by the long RBOT times, and excellent anti-wear properties, as indicated by the small wear scar measurements in a four-ball wear tester (ASTM D2266).

TABLE 3

| Lube composition: | 1-C$_{14}^-$ + PNX | 1-C$_{16}^-$ + PNX | 1-C$_{16}^-$ + DPO |
|---|---|---|---|
| Viscosity at 100° C. (cS) | 7.65 | 7.86 | 4.44 |
| Viscosity at 40° C. | 80.12 | 75.01 | 23.62 |
| Viscosity Index | 33 | 56 | 96 |
| Pour point (C) | −33 | −36 | −50 |
| RBOT (min) | 773 | — | 123 |
| Bromine No. | 1.6 | — | 0.6 |
| Anti-wear properties | | | |
| Wear scar (mm) | 0.864 | 0.606 | 1.9 |
| k (× 10$^8$) | 29.2 | 6.5 | 646 |

1-C$_{14}^-$ + PNX is phenoxathiin alkylated with 1-tetradecene.
1-C$_{16}^-$ + PNX is phenoxathiin alkylated with 1-hexadecene.
1-C$_{16}^-$ + DPO is diphenyloxide alkylated with 1-hexadecene.

The higher sulfurized diphenyloxides isolated in Examples 2 and 7 were mixed with alkylated naphthalene base stock (30% higher SDPOs, 70% alkylated naphthalene (AN) base stock) to illustrate that the higher sulfurized diphenyloxides can be used as a blending component with other low viscosity base stocks to improve viscosity and wear properties. As shown in Table 4, the blends have higher viscosities than the starting base stock. Also, the wear scars of the blends are significantly reduced as compared to the base stock (0.789 mm and 0.864 mm v. 2.1 mm).

TABLE 4

| Lube composition: | Higher SDPOs from Ex. 2 | Higher SDPOs from Ex. 7 | AN base stock |
|---|---|---|---|
| Viscosity at 100° C. (cS) | 6.61 | 6.54 | 4.8 |
| Viscosity at 40° C. (cS) | 49.17 | 53.89 | 27 |
| Viscosity Index | 81 | 58 | 74 |
| Pour point (C) | −38.5 | −40 | −40 |
| Anti-wear properties | | | |
| Wear scar (mm) | 0.864 | 0.789 | 2.1 |
| k (× $10^8$) | 29 | 20.05 | >1000 |

SDPOs = sulfurized diphenyloxides

The use of mixtures of alkylated, sulfurized diphenyloxides in accordance with the present invention for lubricant base stocks was investigated. Four example compositions (Exs. 8–11) were prepared by first sulfurizing diphenyloxide and then alkylating the resulting product mixture. A pre-dried USY powder catalyst (10 g), elemental sulfur powder (2 g, 8 g, 16 g, and 32 g for Examples 8–11, respectively), and diphenyloxide (85 g) were mixed in a 500 cc flask. The mixture was purged with $N_2$ and heated at 250° C. for 3 hours. The temperature of the mixture was then lowered to 220° C. When the temperature of the mixture reached 220° C., 112 g of 1-hexadecene was added over a 3 hour period. The reaction was allowed to proceed for 12 hours. At the end of the reaction, the mixture was cooled to room temperature and the catalyst was removed by filtration. The mixture was then purified to remove unreacted light components by distillation at 130° C. under vacuum (<1 millitorr) for 3 hours.

For comparison purposes, the use of alkylated diphenyloxide was also investigated (Comparative Ex. A). A pre-dried USY catalyst (6 g) and diphenyloxide (85 g) were mixed in a 500 cc flask. The mixture was purged with $N_2$ and heated to 200° C. When the temperature of the mixture reached 200° C., 56 g of 1-hexadecene was added over a 4 hour period. The reaction was allowed to proceed for at least 5 hours at 200° C.

Viscometric, four ball wear, and oxidative stability measurements were made on each of Examples 8–11 and Comparative Ex. A, the results of which are shown in Table 5. The data in Table 5 show that the anti-wear properties of the alkylated, sulfurized diphenyloxides (Exs. 8–11) are significantly improved over those of the alkylated, unsulfurized diphenyloxides (Comparative Ex. A), as indicated by the lower wear scar measurement. Further, the oxidative stability, as measured by high-pressure DSC, was significantly improved for Exs. 8–11. The isothermal induction time at 195° C. was also better in Exs. 8–11 as compared to Comparative Ex. A. Likewise, the DSC induction temperature (i.e., the temperature at which a significant amount of oxidation occurs) was better for Exs. 8–11 than for Comparative Ex. A. Accordingly, the compositions of Exs. 8–11 exhibit much improved oxidative stability and anti-wear properties as compared to Comparative Ex. A.

TABLE 5

| | Example | | | | Comparative |
|---|---|---|---|---|---|
| | 8 | 9 | 10 | 11 | Example A |
| Sulfurization step | | | | | |
| Mole ratio (S/DPO) | 0.125 | 0.5 | 1 | 2 | 0 |
| Temperature (° C.) | 250 | 250 | 250 | 250 | — |
| Wt % USY catalyst | 5 | 5 | 5 | 5 | 3 |
| Alkylation step | | | | | |
| Mole ratio ($C_{16}$/S-DPO) | 1 | 1 | 1 | 1 | 1 |
| Temperature (° C.) | 220 | 220 | 220 | 220 | 200 |
| DPO Conversion | 91 | 87 | 72 | 64 | 98 |
| Wt % selectivity | 98 | 98 | 92 | 90 | 99 |
| Viscometric properties | | | | | |
| Viscosity at 100° C. (cS) | 4.88 | 5.48 | 6.65 | 14.85 | 4.45 |
| Viscosity at 40° C. (cS) | 27.66 | 34.51 | 49.81 | 216.7 | 23.63 |
| Viscosity Index | 98 | 91 | 80 | 58 | 96 |
| Pour point (° C.) | −50 | −48 | −41 | −23 | −49 |
| Four Ball Wear Test | | | | | |
| Wear scar (mm) | 1.081 | 0.672 | 0.731 | 0.65 | 1.856 |
| k (× $10^8$) | 73 | 10 | 14.5 | 8.8 | 646 |
| Oxidative Stability | | | | | |
| by DSC at 195° C. (min) | >100 | >100 | >100 | >100 | 20 |
| Induction temperature (° C.) | 263 | 283 | 290 | 290 | 220, 250 |
| by B10 (617° C., 40 hrs) | | | | | |
| % viscosity increase | 22 | 6 | 9 | | 103 |
| TAN decrease | 4.4 | 0.94 | 1.3 | | 9.2 |
| % lead loss | 35 | 8 | 10 | | 48 |
| Sludge | light | light | trace | | moderate |

The use of mixtures of alkylated, sulfurized diphenyloxides in accordance with the present invention for lubricant base stocks was also investigated (Exs. 12 and 13) by first alkylating diphenyloxide and then sulfurizing the resulting product mixture. A pre-dried USY powder catalyst (10 g) and diphenyloxide (85 g) were mixed in a 500 cc flask. The mixture was purged with $N_2$ and heated at 250° C. for 3 hours. The temperature of the mixture was then lowered to 220° C. When the temperature of the mixture reached 220° C., 112 g of 1-hexadecene was added over a 3 hour period. The reaction was allowed to proceed for 12 hours. For Ex. 12, a 118 g aliquot of the mixture was mixed with 5.7 g of elemental sulfur and 8 g of USY-type catalyst. The mixture was purged with $N_2$ to remove dissolved air and heated to 220° C. for 24 hours. The catalyst was then removed by filtration. A lube fraction was then isolated by distillation at 170° C. under vacuum (1 millitorr). For Ex. 13, a 118 g aliquot of the mixture was mixed with 1.9 g of elemental sulfur and 1.2 g of powder $AlCl_3$ catalyst. The mixture was purged with $N_2$ to remove dissolved air and heated to 80° C. for 24 hours. The reaction was terminated by quenching the catalyst with a 5% NaOH solution.

Viscometric, four ball wear, and oxidative stability measurements were made on each of Examples 12 and 13, the results of which are shown in Table 6. The results for Comparative Ex. A (see above) are also included in Table 6. The data in Table 6 show that Exs. 12 and 13 have significantly lower wear scar diameters and improved oxidative stability, as compared to Comparative Ex. A.

TABLE 6

| | Example | | Comparative |
|---|---|---|---|
| | 12 | 13 | Example A |
| Sulfurization step | | | |
| Mole ratio (ADPO/S) | 1.7 | 5 | 0 |
| Temperature (° C.) | 220 | 80 | 200 |
| Catalyst | USY | $AlCl_3$ | USY |
| Viscometric properties | | | |
| Viscosity at 100° C. (cS) | 4.33 | 4.90 | 4.45 |
| Viscosity at 40° C. (cS) | 23.19 | 27.45 | 23.63 |
| Viscosity Index | 88 | 101 | 96 |
| Pour point (° C.) | −55 | −48 | −49 |
| Four Ball Wear Test | | | |
| Wear scar (mm) | 0.675 | 0.664 | 1.856 |
| k (× $10^8$) | 10.4 | 9.7 | 646 |
| by B10 (617° C., 40 hrs) | | | |
| % viscosity increase | 3 | 2 | 103 |
| TAN decrease | 0.3 | 0.06 | 9.2 |
| Wt % lead loss | 3 | 0.03 | 48 |
| Sludge | moderate | light | moderate |

Those skilled in the art will appreciate that numerous changes and modifications may be made to the preferred embodiments of the invention and that such changes and modifications may be made without departing from the spirit of the invention. It is therefore intended that the appended claims cover all equivalent variations as fall within the true scope and spirit of the invention.

What is claimed is:

1. A method for the production of a sulfurized diphenyloxide comprising a sulfurization step of reacting a diphenyloxide with elemental sulfur in the presence of a solid acid catalyst, wherein the solid acid catalyst is a molecular sieve.

2. The method of claim 1 wherein the sulfurization step produces a product mixture comprising phenoxathiin, and further comprising the step of separating phenoxathiin from the product mixture.

3. The method of claim 1 wherein the sulfurization step produces a product mixture comprising bis(phenyloxide) sulfide, and further comprising the step of separating bis (phenyloxide) sulfide from the product mixture.

4. The method of claim 1 wherein the dipehnyloxide is alkylated.

5. The method of claim 4 wherein the sulfurization step produces a product mixture comprising an alkylated phenoxathiin, and further comprising the step of separating the alkylated phenoxathiin from the product mixture.

6. The method of claim 1 wherein the solid acid catalyst comprises a zeolite.

7. The method of claim 7 wherein the sulfurization step is conducted at a temperature above about 75° C.

8. The method of claim 1 comprising the step of reacting the diphenyloxide with an alkylating agent.

9. The method of claim 8 wherein the alkylating agent is an olefin.

10. The method of claim 8 wherein the alkylating step and the sulfurization step are performed substantially concurrently.

11. The method of claim 8, wherein the alkylating step and the sulfurization step are performed substantially sequentially.

12. The method of claim 1, wherein the molecular sieve comprises a non-zeolite molecular sieve.

13. The method of claim 1, wherein the molecular sieve comprises a large pore molrcular sieve.

14. A method for producing a stock solution, the method comprising the steps of reacting a diphenyloxide with elemental sulfur in the presence of a solid acid catalyst; and reacting the diphenyloxide with an alkylating agent to produce the stock solution, wherein the solid acid catalyst is a molecular sieve.

15. The method of claim 14 wherein the alkylating step and the sulfurization step are performed substantially concurrently.

16. The method of claim 14 wherein the alkylating step and the sulfurization step are performed substantially concurrently.

17. The method of claim 14, wherein the molecular sieve comprises a non-zeolite molecular sieve.

18. The method of claim 14, wherein the molecular sieve comprises a large pore molecular sieve.

19. A composition comprising, in weight percent, about:

| | |
|---|---|
| Diphenyloxide | 40–80 |
| Diphenyloxide thiol | 0–15 |
| Phenoxathiin | 5–45 |
| Bis(diphenyloxide) sulfide + | 3–50. |

| -continued |
|---|
| Diphenyloxide phenoxathiin sulfide + Bis(phenoxathiin) sulfide |

20. A method for producing a stock solution, the method comprising the steps of reacting a diphenyloxide with elemental sulfur in the presence of a solid acid catalyst; and reacting the diphenyloxide with an alkylating agent to produce the stock solution.

21. The method of claim 20, wherein the sulfurization step and the alkylating step are performed substantially sequentially.

22. The method of claim 20, wherein the solid acid catalyst comprises a non-zeolite molecular sieve.

23. The method of claim 20, wherein the solid acid catalyst comprises a large pore molecular sieve.

* * * * *